United States Patent [19]

Vonlanthen et al.

[11] Patent Number: 4,778,898

[45] Date of Patent: Oct. 18, 1988

[54] TRISIMIDES OF ALLYL-SUBSTITUTED OR METHALLYL-SUBSTITUTED BICYCLO[2.2.1]HEPT-5-ENE-2,3-DICARBOXIMIDES AND THE USE THEREOF

[75] Inventors: Christian Vonlanthen, Ependes; Andreas Kramer, Düdingen; Alfred Renner, Muntelier, all of Switzerland

[73] Assignee: Ciba-Geigy Corporation, Ardsley, N.Y.

[21] Appl. No.: 921,914

[22] Filed: Oct. 22, 1986

[30] Foreign Application Priority Data

Oct. 25, 1985 [CH] Switzerland ............... 4610/85

[51] Int. Cl.$^4$ ............................................. C07D 209/48
[52] U.S. Cl. ............................ 548/415; 528/321; 528/322; 548/435
[58] Field of Search .................... 548/415, 435

[56] References Cited

U.S. PATENT DOCUMENTS

| | | | |
|---|---|---|---|
| 3,960,812 | 6/1976 | Renner et al. | 548/413 |
| 4,003,862 | 1/1977 | Albright | 548/415 |
| 4,225,497 | 9/1980 | Baudouin et al. | 548/415 |
| 4,395,557 | 7/1983 | Varma et al. | 548/415 |
| 4,515,962 | 5/1985 | Renner | 548/435 |
| 4,604,437 | 8/1986 | Renner | 548/435 |

*Primary Examiner*—Mary E. Ceperley
*Attorney, Agent, or Firm*—Harry Falber; Edward McC. Roberts

[57] ABSTRACT

Compounds of formula

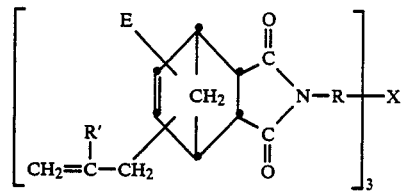

wherein
E and R' are each independently of the other a hydrogen atom or a methyl group,
X is

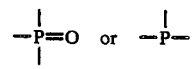

and R is —$C_mH_{2m}$—, in which m is 2 to 20, —$C_nH_{2n}O$—, in which n is 2 to 6, m- or p-phenylene, m- or p-oxyphenylene, in which the oxygen atom is attached to the group X, or X is

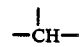

and R is m- or p-phenylene, or X is

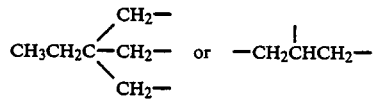

and R is —$(CH_2CH_2O)_q$—, —$(CH_2CH_2CH_2O)_q$— or —$[CH_2CH(CH_3)O]_q$—, in which q is 1 to 6, m- or p-oxyphenylene, in which the oxygen atom is attached to the group X, or X is

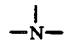

and R is —$C_rH_{2r}$—, in which r is 2 to 4, or m- or p-phenylene,
are suitable for the preparation of crosslinked polymers.

8 Claims, No Drawings

TRISIMIDES OF ALLYL-SUBSTITUTED OR METHALLYL-SUBSTITUTED BICYCLO[2.2.1]HEPT-5-ENE-2,3-DICARBOXIMIDES AND THE USE THEREOF

The present invention relates to novel trisimides of allyl-substituted or methallyl-substituted bicyclo[2.2.1]hept-5-ene-2,3-dicarboximides, to a process for their preparation, and to the use thereof for the preparation of polymers by heating.

Allyl-substituted or methallyl-substituted [methyl]-bicyclo[2.2.1]hept-5-ene-2,3-dicarboximides from which crosslinked polymers can be prepared by heating are disclosed in European published patent specifications Nos. 0 105 024 A1 and 0 152 372 A2. Unsaturated trisimides, especially trismaleimides, of aromatic aminophosphates and aminophosphites are also disclosed in German Offenlegungsschrift No. 23 50 472.

The present invention relates to compounds of formula I

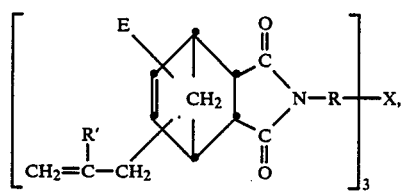

wherein
E and R' are each independently of the other a hydrogen atom or a methyl group,
X is

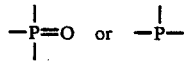

and R is —$C_mH_{2m}$—, in which m is 2 to 20, $C_nH_{2n}O$—, in which n is 2 to 6, m- or p-phenylene, m- or p-oxyphenylene, in which the oxygen atom is attached to the group X, or
X is

and R is m- or p-phenylene, or X is

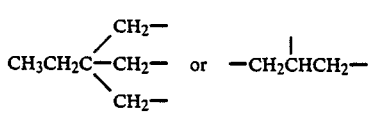

and R is —($CH_2CH_2O$)$_q$—, —($CH_2CH_2CH_2O$)$_q$— or —[$CH_2CH(CH_3)O$]$_q$—, in which q is 1 to 6, m- or p-oxyphenylene, in which the oxygen atom is attached to the group X, or
X is

and R is —$C_rH_{2r}$—, in which r is 2 to 4, or m- or p-phenylene.

R as —$C_mH_{2m}$— or —$C_nH_{2n}$—O— may be straight chain or branched alkylene or oxyalkylene groups. Examples of such groups are: 1,2-ethylene, 1,3- and 1,2-propylene, tetramethylene, pentamethylene, 2,2-dimethyl-1,3-propylene, hexamethylene, heptamethylene, octamethylene, decamethylene, dodecamethylene, tetradecamethylene, pentadecamethylene, hexadecamethylene, octadecamethylene and eicosylene; oxyethylene, 1,2-oxypropylene, n-oxybutylene, n-oxypentylene or n-oxyhexylene. Preferred groups are straight chain —$C_mH_{2m}$— or —$C_nH_{2n}$— groups, wherein m is 2 or 6 and, preferably, 2 to 4, carbon atoms, and n is 2 to 4 carbon atoms.

Where R is —($CH_2CH_2O$)$_q$—, —($CH_2CH_2CH_2O$)$_q$— or —($CH_2CH(CH_3)O$)$_q$—, the value of q may be different in each of the definitions of R. Preferably the values of q are on average from 1.2 to 3, most preferably from 1.2 to 2.

R as a —$C_rH_{2r}$— group may be a straight chain or branched radical such as 1,2-ethylene, 1,3- or 1,2-propylene and 1,4-butylene. —($CH_2$)$_r$— groups, in which r is 2 or 3, are preferred.

Each of E and R' is preferably a hydrogen atom. X is preferably

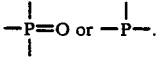

Particularly preferred compounds of formula I are those wherein X is

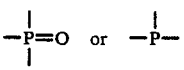

and R is —($CH_2$)$_m$—, in which m is 2 to 4, m- or p-phenylene or m- or p-oxyphenylene.
When X is

R is preferably p-phenylene. A further class of preferred compounds of formula I comprises those wherein X is

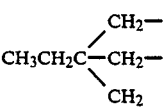

and each R is —[$CH_2CH(CH_3)O$]$_q$—, in which the value of q is on average from 1.2 to 3, preferably from 1.2 to 2, as well as compounds of formula I, wherein X is

and each R is —($CH_2CH_2O$)$_q$—, wherein the the value of q is on average from 1.2 to 3, preferably from 1.2 to 2, and is most preferably m- or p-oxyphenylene. When X is

R is preferably —(CH$_2$)$_r$—, in which r is 2 or 3, or m- or p-phenylene.

The compounds of formula I can be prepared in a manner known per se by reacting a compound of formula II

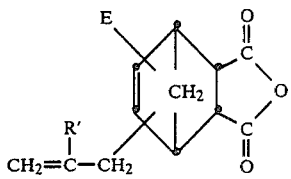

with a compound of formula III

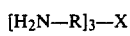                      (III)

in which formulae E, R, R' and X are as defined above, at elevated temperature and with removal of the water of reaction by distillation.

The reaction can be carried out without a solvent or in the presence of an inert solvent which can be used for the azeotropic removal of the water of reaction (entrainer such as toluene and xylene). The temperatures for the reaction in the presence of a solvent can be in the range from 100° C. to reflux temperature. The reaction in the melt conveniently takes place at atmospheric pressure in the temperature range from 100° to 250° C., preferably from 130° to 220° C. The reaction in the presence of an inert solvent is preferred.

Compounds of formula I, wherein X is

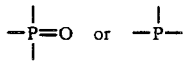

and R is —C$_n$H$_{2n}$—O— or m- or p-oxyphenylene, can also be obtained by a modified process by reacting a compound of formula IV

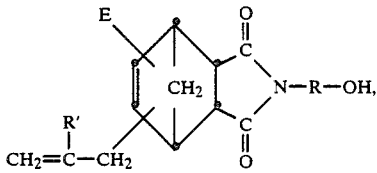

wherein E and R' are as defined for formula I and R is —C$_n$H$_{2n}$— or m- or p-phenylene, with a phosphoroxy halide or a phosphorus trihalide, preferably phosphoroxy chloride, phosphorus tribromide or phosphorus trichloride, in the presence of a base in the molar ratio of at least 1:3.

Examples of suitable bases are tertiary amines such as triethylamine, tri-n-butylamine, pyridine and dimethyl aniline. This reaction is conveniently carried out in an inert organic solvent such as toluene or xylene, in the temperature range from −50° to +50° C., preferably from 0° to 30° C.

When X is

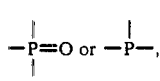

the concurrent use of an antioxidant may be expedient in the above reactions in the presence of an inert solvent.

The compounds of formulae II, III and IV are known or they can be prepared by methods known per se. Compounds of formula II may be obtained e.g. by the process described in U.S. Pat. No. 3,105,839, by reacting sodium cyclopentadienide or sodium methylcyclopentadienide with an allyl or methallyl halide, followed by a Diels-Alder reaction with maleic anhydride. Although it is stated in the U.S. patent specification that the allyl group is located in the 7-position of the bicyclic system, recent investigations have shown that a mixture of isomers is formed with respect to the position of the allyl or methallyl group (in 1- and 6-position) and also with respect to the endo- and exo-configuration of the anhydride moiety. Compounds of formula IV can be prepared by reacting an anhydride of formula II with the corresponding amino alcohols H$_2$N—R—OH, which reaction is likewise carried out at elevated temperature and with removal of the water of reaction by distillation. Compounds of formula III, wherein X is

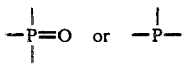

can be obtained e.g. by reacting amino alcohols H$_2$N—R—OH with phosphoroxy halides or phosphorus trihalides.

The compounds of formula I are generally obtained in the form of solid resins which can be polymerized to crosslinked products with high glass transition temperatures. They have versatile application, e.g. as heat-resistant adhesives, as insulating materials in electronics and electrical engineering and, first and foremost, as matrix resins for composites. The trisimides of formula I can be polymerised alone or together with other unsaturated imides, e.g. those of the kind described in published European patent applications Nos. 0 105 024 A1 and 0 152 372 A2. The polymerisation is conveniently carried out in the temperature range from 180° to 300° C., preferably from 200° to 260° C. The reaction times are generally from 6 to 50, preferably from 6 to 20, hours. It can also on occasion be advantageous to carry out the polymerisation in two steps by first carrying out a pregelation at fairly low temperature, e.g. in the range from 180° to 220° C., and subsequently bringing the polymerisation to completion at elevated temperature, e.g. in the range from 240° to 300° C.

Hence the invention also relates to polymers which can be obtained by heating a trisimide of formula I to temperatures in the range from 180° to 300° C.

The trisimides of formula I are very reactive. Despite their high reactivity, however, they are generally still fusible and pourable. The polymers prepared from the compounds of formula I have useful properties, especially good mechanical and, in particular, good heat resistance such as glass transition and decomposition temperatures and insignificant weight loss at elevated temperatures. Polymers prepared from trisimides of formula I, wherein X is

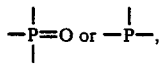

also find utility as self-quenching plastics.

EXAMPLE 1

Preparation of the N,N',N''-tris(allylbicyclo[2.2.1]hept-5-ene-2,3-dicarboximide) of tris(4-aminophenyl)phosphate 204 g of allylbicyclo[2.2.1]hept-5-ene-2,3-dicarboxylic anhydride (allylnadic anhydride, prepared in accordance with U.S. Pat. No. 3,105,839), 109.1 g of 4-aminophenol, 0.16 g of the compound of formula

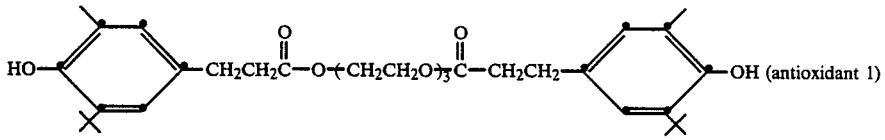

are heated to the boil in 500 g of a mixture of xylene isomers. The water of reaction is removed by means of a Hahn distillation head. The reaction is complete after 5 hours at 120°–123° C. The reaction mixture is clarified by filtration (through a Hyflo-Supercel filter), then 111.3 g of triethylamine are added and, after cooling to 0° C., 51 g of phosphoroxy chloride are added dropwise over 1 hour with stirring and external cooling. The reaction mixture is stirred overnight at room temperature, the pH is adjusted to 6 with 50 ml of HCl, and the precipitated triethylamine hydrochloride is dissolved in 400 ml of water. The xylene solution is washed with 2×600 ml of water, dried over $Na_2SO_4$, concentrated by rotary evaporation and kept for 1 hour at 1700 Pa and 150° C., to give 263.5 g (85% of theory) of the N,N',N''-tris(allylbicyclo)[2.2.1]hept-5-ene-2,3-dicarboximide of tris(4-aminophenyl)phosphate in the form of a reddish brown solid resin with a glass transition temperature of 66.5° C.

Elemental analysis for $C_{54}H_{48}N_3O_{10}P$:

| theory | C 69.74% | H 5.20% | N 4.52% | P 3.33% |
|---|---|---|---|---|
| found | C 69.31% | H 5.39% | N 4.22% | P 3.45%. |

IR-spectrum: 1201 cm$^{-1}$ phosphonyl group, 1620 cm$^{-1}$ cyclic double bond, 1640 cm$^{-1}$ allyl group, 1710 cm$^{-1}$ and 1776 cm$^{-1}$ for the carbonyl group.

EXAMPLE 2

61.2 g of allylnadic anhydride and 37.1 g of tris(4-aminophenyl)phosphate (m.p. 152°–155° C., prepared in accordance with U.S. Pat. No. 3,415,779, compound 1) are mixed and heated at 1.06 Pa to 155° C. with stirring. The resultant reddish brown resin is poured into a metal cup. The resin (the compound is identical with that of Example 1) congeals immediately. It has a glass transition temperature of 67° C. Yield: 93 g (quantitative).

Elemental analysis for $C_{54}H_{48}N_3O_{10}P$:

| theory | C 69.74% | H 5.20% | N 4.52% | P 3.33% | free amine 0% |
|---|---|---|---|---|---|
| found | C 69.41% | H 5.20% | N 4.49% | P 3.37% | free amine 0.07%. |

The IR spectrum accords with the spectrum of the compound obtained in Example 1.

EXAMPLE 3

Preparation of the N,N',N''-tris(allylbicyclo[2.2.1]hept-5-ene-2,3-dicarboximide) of tris(3-aminophenyl)phosphite N-(3'-hydroxyphenyl)allylbicyclo[2.2.1]hept-5-ene-2,3-dicarboximide is prepared by azeotropic distillation of a reaction mixture consisting of 306 g of allylnadic anhydride, 163.7 g of 3-aminophenol and 750 g of xylene. The solvent is removed by distillation, affording as residue 330.4 g of a reddish brown resin with a glass transition temperature (Tg) of 60° C. 324.5 g of this intermediate are dissolved in 750 g of toluene, 122.45 g of triethylamine are added and 50.3 g of phosphorus trichloride are added dropwise with stirring and external cooling such that the temperature remains between 7° and 11° C. The reaction mixture is stirred overnight, neutralised with 1N HCl and washed twice with water. The toluene phase is dried over $Na_2SO_4$, filtered, and concentrated by rotary evaporation (150° C./1600 Pa), affording 219.4 g (72% of theory) of the N,N',N''-tris-(allylbicyclo[2.2.1]hept-5-ene-2,3-dicarboximide) of tris(3-aminophenyl)phosphite in the form of a dark solid resin; Tg=55° C.

Elemental analysis for $C_{54}H_{48}N_3O_9P$:

| theory | C 70.96% | H 5.29% | N 4.60% | P 3.39% |
|---|---|---|---|---|
| found | C 71.42% | H 5.70% | N 4.27% | P 3.30%. |

EXAMPLE 4

Preparation of the N,N',N''-tris(allylbicyclo[2.2.1]hept-5-ene-2,3-dicarboximide) of tris(3-aminophenyl)phosphite oxide A solution of 55.1 g of allylnadic anhydride, 29 g of tris(3-aminophenyl)phosphine oxide (m.p. 251°–254° C.) and 42 g of antioxidant 1 in 159 g of xylene is heated to the boil and the water formed during the imidisation is distilled off through a Dean-Stark separator. Before recycling, the distillate is passed for 3 hours over granulated calcium chloride, cooled, and clarified by filtration. The xylene is distilled off by rotary evaporation under vacuum at 140° C., affording 78.0 g (98.4% of theory) of the N,N',N''-tris(allylbicyclo[2.2.1]hept-5-ene-2,3-dicarboximide) with a glass transition temperature of 95.5° C.

Elemental analysis for $C_{54}H_{48}O_7N_3P$:

| theory | C 73.54% | H 5.49% | N 4.76% | P 3.51% |
|---|---|---|---|---|
| found | C 71.69% | H 5.75% | N 4.65% | P 3.31%. |

EXAMPLE 5

Preparation of the N,N',N''-tris(allylbicyclo[2.2.1]hept-5-ene-2,3-dicarboximide) of a polyoxypropylenetriamine 61.2 g of allylnadic anhydride and 45.8 g of a polyoxypropylenetriamine with an average molecular weight of 403 of formula

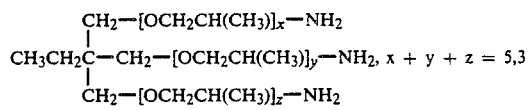

(Jeffamine T 403 ®, ex Texaco) are heated to 200° C., then the pressure is lowered to 6.7 Pa and these conditions are kept for 5 hours. The N,N',N''-tris(allylbicyclo[2.2.1]hept-5-ene-2,3-dicarboximide) of polyoxypropylenetriamine is obtained as a pale brown resin in quantitative yield. The resin has a viscosity of 1.817 Pa.s at 120° C.

EXAMPLE 6

Preparation of the N,N',N''-tris(allylbicyclo[2.2.1]hept-5-ene-2,3-dicarboximide) of tris(2-aminoethyl)amine 21.0 g of allylnadic anhydride and 5.0 g of tris(2-aminoethyl)amine are added to 200 ml of toluene and the mixture is heated under reflux for 5 hours on a water separator. The toluene is distilled off by rotary evaporation at 60° C. under vacuum and the residue is dried under a high vacuum at 130° C., affording 23.5 g (98% of theory) of the N,N',N''-tris(allylbicyclo[2.2.1]hept-5-ene-2,3-dicarboximide) of tris(2-aminoethyl)amine in the form of a reddish brown resin which is solid at room temperature and has a glass transition temperature of 83.5° C.

Elemental analysis for $C_{42}H_{48}N_4O_6$:

| theory | C 71.57% | H 6.86% | N 7.95% |
|---|---|---|---|
| found | C 70.82% | H 6.77% | N 7.76%. |

Infrared spectrum: 1640 cm$^{-1}$ allyl group, 1700 cm$^{-1}$ carbonyl group.

A 12 hour polymerisation of the above compound at 250° C. yields a solid with a glass transition temperature above 300° C.

EXAMPLE 7

Preparation of the N,N',N''-tris(allylbicyclo[2.2.1]hept-5-ene-2,3-dicarboximide) of tris(4-aminophenyl)amine A suspension of 43.7 g of allylnadic anhydride and 21.6 g of tris(4-aminophenyl)amine in 400 ml of toluene is heated to 100° C., whereupon the trisamine only partially dissolves. Addition of 20 ml of N,N-dimethylformamide gives a clear reddish brown reaction solution which is then boiled for 4½ hours on a water separtator. The solvent is subsequently removed by rotary evaporation and the residue is dried under a high vacuum at 130° C., affording 590.0 g of the N,N',N''-tris(allylbicyclo[2.2.1]hept-5-ene-2,3-dicarboximide) of tris(4-aminophenylene)amine in the form of a brown solid resin with a glass transition temperature of 67° C. and a melt interval of 155°–157° C.

Elemental analysis for $C_{54}H_{48}N_4O_6$:

| theory | C 76.40% | H 5.70% | N 6.60% |
|---|---|---|---|
| found | C 74.80% | H 5.9% | N 6.9%. |

Infrared spectrum: 1640 cm$^{-1}$ allyl group, 1720 cm$^{-1}$ carbonyl group.

A 12 hour polymerisation of the above compound at 250° C. affords a solid with a Tg above 300° C.

EXAMPLE 8

Preparation of the N,N',N''-tris(allylbicyclo[2.2.1]hept-5-ene-2,3-dicarboximide) of 1,2,3-tris(4-aminophenoxy)propane Following the procedure of Example 6, 52.8 g of allylnadic anhydride and 31.5 g of 1,2,3-tris(4-aminophenyl)propane are reacted in 400 ml of toluene, to give 74.9 g (94% of theory) of the above trisimide in the form of a reddish brown solid resin with a glass transition temperature of 94° C. and a melt interval of 130°–160° C.

Elemental analysis for $C_{57}H_{56}O_9N_3$:

| theory | C 73.86% | H 6.04% | N 4.53% |
|---|---|---|---|
| found | C 73.10% | H 5.82% | N 4.42%. |

Infrared spectrum: 1710 cm$^{-1}$ carbonyl group.

A 12 hour polymerisation of the above trisimide at 250° C. affords a solid with a glass transition temperature above 300° C.

EXAMPLE 9

Preparation of the N,N',N''-tris(allylbicyclo[2.2.1]hept-5-ene-2,3-dicarboximide) of tris(2-aminoethyl)phosphate N-(2'-hydroxyethyl)allylbicyclo[2.2.1]hept-5-ene-2,3-dicarboximide is prepared by azeotropic distillation of a reaction mixture consisting of 51 g of allylnadic anhydride, 15.3 g of 2-aminoethanol and 150 g of toluene. The solvent is removed by distillation, affording as residue 61 g of a colourless viscous oil. 55.1 g of this intermediate are dissolved in 200 g of toluene, 24.8 g of triethylamine are added and 11.3 g of phosphoroxy chloride are added dropwise with stirring and external cooling such that the temperature remains between 0° and 5° C. The reaction mixture is stirred overnight, neutralised with 1N HCl and washed with water. The toluene phase is dried over $Na_2SO_4$ and filtered, and the solvent is distilled off by rotary evaporation at 90° C. under vacuum, affording 52.5 g (89.9% of theory) of a yellowish brown resin which is still just liquid at room temperature. $\eta_{80}$: 3407 mPa.s.

Elemental analysis for $C_{42}H_{48}O_{10}N_3P$:

| theory | C 64.19% | H 6.16% | N 5.35% | P 3.94% |
|---|---|---|---|---|
| found | C 64.11% | H 6.28% | N 5.27%. | P 3.86%. |

USE EXAMPLES I–V

The trisimides obtained in Examples 1, 3, 4 and 5 are poured direct from the reaction mass into steel moulds measuring 12×12×0.4 cm, pre-gelled for 3 hours at 200° C. and 3 hours at 220° C., cured for 12 hours at 250° C. and cut into specimen bars. In the same manner, 80 g of a 1:1 mixture of the trisimide obtained in Example 2 and N,N'-hexamethylenebis(allylbicyclo[2.2.1]hept-5-ene-2,3-dicarboximide) [prepared in accordance with Example 9 of European patent application EP-A No. 0 105 024] is poured into steel moulds, subjected to pregelation, cured and cut into specimen bars. The test results are reported in the following table.

USE EXAMPLE VI 80 g of a 1:1 mixture of the trisimide obtained in Example 1 and N-allylimide allylbicyclo[2.2.1]hept-5-ene-2,3-dicarboximide (prepared in accordance with Example 3 of EP-A No. 0 105 024) are poured as hot resin into a steel mould measuring 12×12×0.4 cm and pre-gelled for 3 hours at 200° and 3 hours at 220° C., and cured for 12 hours at 250° C.

USE EXAMPLE VII 80 g of a 3:3:4 mixture of the trisimide obtained in Example 1, N,N'-4,4'-diphenylmethanebismaleimide and N-allyl allylbicyclo[2.2.0]hept-5-ene-2,3-dicarboximide are poured as hot resin into a steel mould measuring 12×12×0.4 cm and pre-gelled for 3 hours at 200° C. and for 3 hours at 220° C. and cured for 12 hours at 250° C.

|                              | VI    | VII   |
|------------------------------|-------|-------|
| Flexural strength (N/mm$^2$) | 63.5  | 78.1  |
| elongation (%)               | 1.9   | 2.3   |
| impact strength (hJ/m$^2$)   | 4.0   | 5.0   |
| Tg (°C.)                     | 284   | 321   |

TABLE

| Use Example | I | II | III | IV | V | VI | VII |
|---|---|---|---|---|---|---|---|
| Resin of Example | 1 | 3 | 4 | 5 | 2* | 1 | 1 |
| bending strength according to DIN 53452 N/mm$^2$ | 91.6 | not pourable | not pourable | 97.2 | 98.2 | 63.5 | 78.1 |
| elongation according to ISO 178 (%) | 3.1 | — | — | 4.8 | 3.8 | 1.9 | 2.3 |
| impact strength DIN 53455 (kJ/m$^2$) | 8.6 | — | — | 8.4 | 11.3 | 4.0 | 5.0 |
| Tg of the resin (°C.) | 311 | 250 | 310 | 150 | 279 | 284 | 321 |
| onset of decomposition of the resin (°C.) | 340 | 250 | 330 | n.d. | n.d. | | |
| 10% weight loss at °C. | 390 | 389 | 439 | 397 | n.d. | | |
| combustibility according to UL 94 step | 0 | 0 | 0 | 1 | 0 | | |
| water absorption after 1 h at 100° C. (%) | 0.64 | n.d. | n.d. | 0.76 | 0.59 | | |

*1:1 mixture with N,N'—hexamethylene-bis(allylbicyclo[2.2.1]hept-5-ene-2,3-dicarboximide).
n.d. = not determined

What is claimed is:

1. A compound of formula I

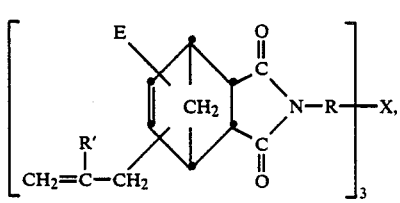

wherein

E and R' are each independently of the other a hydrogen atom or a methyl group,

X is

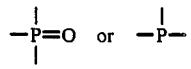

and R is —$C_mH_{2m}$—, in which m is 2 to 20, —$C_nH_{2n}O$—, in which n is 2 to 6, m- or p-phenylene, m- or p-oxyphenylene, in which the oxygen atom is attached to the group X, or X is

and R is m- or p-phenylene, or X is

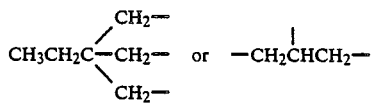

and R is —$(CH_2CH_2O)_q$—, —$(CH_2CH_2CH_2O)_1$— or —$[CH_2CH(CH_3)O]_q$—, in which q is 1 to 6, m- or p-oxyphenylene, in which the oxygen atom is attached to the group X, or X is

and R is —$C_rH_{2r}$—, in which r is 2 to 4, or m- or p-phenylene.

2. A compound of formula I according to claim 1, wherein each of E and R' is a hydrogen atom.

3. A compound of formula I according to claim 1, wherein X is

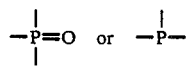

and R is —$(CH_2)_m$—, in which m is 2 to 4, m- or p-phenylene or m- or p-oxyphenylene.

4. A compound of formula I according to claim 1, wherein X is

and R is p-phenylene.

5. A compound of formula I according to claim 1, wherein X is

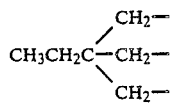

and each R is —[CH$_2$CH(CH$_3$)O]$_q$—, in which the value of q is on average from 1.2 to 3.

6. A compound of formula I according to claim 1, wherein X is

and each R is —(CH$_2$CH$_2$O)$_q$—, wherein the the value of q is on average from 1.2 to 3, or is m- or p-oxyphenylene.

7. A compound of formula I according to claim 1, wherein X is

—N—
| and R is —(CH$_2$)$_r$—, in which r is 2 or 3, or is m- or p-phenylene.

8. A compound according to claim 1 of formula I, wherein each of E and R' is a hydrogen atom, X is

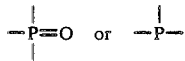

and R is p-oxyphenylene.

* * * * *